US006869400B2

(12) United States Patent
Miyaki

(10) Patent No.: US 6,869,400 B2
(45) Date of Patent: Mar. 22, 2005

(54) MEDICAL UNIT

(75) Inventor: Hironaka Miyaki, Hachioji (JP)

(73) Assignee: Olympus Corporation, Tokyo (JP)

( * ) Notice: Subject to any disclaimer, the term of this patent is extended or adjusted under 35 U.S.C. 154(b) by 361 days.

(21) Appl. No.: 09/809,681

(22) Filed: Mar. 15, 2001

(65) Prior Publication Data

US 2001/0023318 A1 Sep. 20, 2001

(30) Foreign Application Priority Data

Mar. 16, 2000 (JP) .......................................... 2000-074520

(51) Int. Cl.[7] .............................. A61B 8/14; A61B 5/02
(52) U.S. Cl. ...................................... 600/437; 600/528
(58) Field of Search ................................. 600/437, 407, 600/444, 528, 447, 496, 440, 443; 73/584, 648; 181/101, 123, 125; 367/87, 7, 118

(56) References Cited

U.S. PATENT DOCUMENTS

| | | | | |
|---|---|---|---|---|
| 4,237,901 A | * | 12/1980 | Taenzer | 600/443 |
| 4,444,197 A | * | 4/1984 | Koyano et al. | 600/443 |
| 4,671,104 A | * | 6/1987 | Fischer | 73/81 |
| 5,333,498 A | * | 8/1994 | Brackett et al. | 73/304 R |
| 5,402,793 A | * | 4/1995 | Gruner et al. | 600/447 |
| 5,511,425 A | * | 4/1996 | Kleinert et al. | 73/627 |
| 5,841,448 A | * | 11/1998 | Moriyama et al. | 347/19 |
| 6,066,096 A | * | 5/2000 | Smith et al. | 600/439 |
| 6,117,084 A | * | 9/2000 | Green et al. | 600/459 |
| 6,589,173 B1 | * | 7/2003 | Mitragotri | 600/437 |
| 6,622,542 B2 | * | 9/2003 | Derek et al. | 73/19.03 |

FOREIGN PATENT DOCUMENTS

| | | |
|---|---|---|
| JP | 5-245140 | 9/1993 |
| JP | 8-252250 | 10/1996 |
| JP | 9-028705 | 2/1997 |
| JP | 10-221317 | 8/1998 |
| JP | 11-056852 | 3/1999 |

* cited by examiner

*Primary Examiner*—Daniel Robinson
(74) *Attorney, Agent, or Firm*—Scully, Scott, Murphy & Presser

(57) ABSTRACT

A medical unit including a unit main body having an upper face and a circuit therein. The unit main body further including an input means arranged on the upper face and connected to the circuit, and a connected section arranged on the upper face to which the connector section of an external device is connected. Preferably, the medical unit includes: an ultrasonic probe having a probe element at its distal end and an electrical connection section at its proximal end; and an ultrasonic diagnostic unit main body having an upper face and a circuit therein for processing ultrasonic signals transmitted from said ultrasonic probe element, said ultrasonic unit main body further including an input means arranged on said upper face and connected to said circuit, and a connected section arranged on said upper face to which said electrical connection section is connected.

8 Claims, 3 Drawing Sheets

MEDICAL UNIT

CROSS-SECTION TO RELATED APPLICATIONS

This application claims benefit of Japanese Application No. 2000-74520 filed on Mar. 16, 2000, the contents of which is incorporated by this reference.

BACKGROUND OF THE INVENTION

1. Field of the Invention

The present invention relates to a medical unit used with plural external devices connected to the main body of the unit. More particularly, the present invention relates to an ultrasonic medical diagnostic unit used with an ultrasonic probe connected to the ultrasonic diagnostic unit main body.

2. Prior Art

Traditionally, a variety of ultrasonic diagnostic units have been proposed. Generally speaking, an ultrasonic diagnostic unit can display ultrasonic tomographic images, two-dimensional visible ones, by repeatedly transmitting an ultrasonic pulse from the ultrasonic probe element to the inside of a living body tissue, and receiving the echo of the ultrasonic pulse via the same or another probe element. Those ultrasonic diagnostic images are used for diagnosis of diseases, for example.

For those ultrasonic diagnostic units, an external ultrasonic probe is typically used. However, an internal ultrasonic probe is also used with an endoscope. The internal ultrasonic probe has an elongated insertion section which can be introduced into a body cavity through an endoscope forceps insertion channel, for example. With such an endoscope system, ultrasonic tomographic images of the subject region including a lesion such as a cancerous mucosal tissue or polyp can be viewed through the endoscope.

In recent years, a variety of ultrasonic probes for three-dimensional scanning have been proposed to obtain three-dimensional images. With such an ultrasonic probe for three-dimensional scanning, the shape of a tumor on the subject can be understood, and its volume can be measured.

In this way, various ultrasonic probes can be used for ultrasonic diagnosis. For example, Japanese Patent Application Publication 5-245140 discloses an ultrasonic diagnostic unit by which plural ultrasonic probes can be controlled. This ultrasonic diagnostic unit has a case with which ultrasonic probe elements for transmitting and receiving ultrasonic waves are covered, and on which a grip section is arranged to be gripped by a hand. On the grip section, a sensor is attached to transmit a signal when it is gripped. Through the output of the sensor, the selected ultrasonic probe element can be recognized. And, operation conditions can be automatically switched on the side of the main body of the ultrasonic diagnostic unit according to the specifications of the selected ultrasonic probe element. Such a configuration allows the diagnostician to reduce wasteful actions and to increase the efficiency of diagnosis without manipulating the main body of the ultrasonic diagnostic unit.

However, the ultrasonic diagnostic unit disclosed in the above-mentioned 5-245140 publication must be configured in such a way that plural ultrasonic search elements can be connected to the ultrasonic diagnostic unit main body. In addition, the surgeon must select an ultrasonic search element for his or her diagnostic purpose. As a result, the ultrasonic diagnostic unit main body must be large enough to accommodate such plural ultrasonic search elements.

On the other hand, there also exist small-sized or medium-sized ultrasonic diagnostic units in which only a single ultrasonic probe can be connected to the main body. In order to use such an ultrasonic diagnostic unit with various ultrasonic probes, it is necessary to connect the connector of each of them to the ultrasonic diagnostic unit main body each time. Since in many cases, the connector is connected in an inconvenient place, for example, the reverse side of the ultrasonic diagnostic unit, or a lower place at the feet, it is troublesome to replace it.

SUMMARY OF THE INVENTION

An object of the present invention is to provide a medical unit in which external devices connected thereto can be easily replaced.

Another object of the present invention is to provide a medical unit in which external devices connected thereto can be easily identified.

Accordingly, a medical unit is provided. The medical unit comprises a unit main body having an upper face and a circuit therein, said unit main body further including an input means arranged on said upper face and connected to said circuit, and a connected section arranged on said upper face to which the connector section of an external device is connected.

In a preferred implementation of the medical unit of the present invention, the medical unit comprises: an ultrasonic probe having a probe element at its distal end and an electrical connection section at its proximal end; and an ultrasonic diagnostic unit main body having an upper face and a circuit therein for processing ultrasonic signals transmitted from said ultrasonic probe element, said ultrasonic unit main body further including an input means arranged on said upper face and connected to said circuit, and a connected section arranged on said upper face to which said electrical connection section is connected.

Preferably, said ultrasonic probe further includes a probe upper face which is turned upward when said electrical connection section is connected to said connected section, and an identifying means which is arranged on said probe upper face so that the kind of said ultrasonic probe can be identified by visual inspection. Said ultrasonic diagnostic unit main body preferably has a cover with which said connected section is covered in which said connected section can be covered with said cover while said electric connection section is connected to said connected section. At least a portion of said cover is transparent and corresponds to said identifying means when said cover covers said connected section.

More preferably, said ultrasonic diagnostic unit main body has a control section for controlling the passage of electric current to said connected section, said control section passing electric current to said connected section when said connected section is covered with said cover, and stopping electric current to said connected section when said connected section is not covered with said cover.

Still yet more preferably, the medical unit of the present invention includes a display means for displaying ultrasonic diagnostic images from said ultrasonic probe element and electrically connected to said ultrasonic diagnostic unit main body via a signal cable.

In a further preferred implementation of the medical unit of the present invention, said connector section is attached to and removed from said connected section in a direction substantially vertical to said upper face.

BRIEF DESCRIPTION OF THE DRAWINGS

These and other features, aspects, and advantages of the apparatus of the present invention will become better understood with regard to the following description, appended claims, and accompanying drawings where:

FIG. 1 illustrates the medical unit configured as an ultrasonic diagnostic unit;

FIG. 2 illustrates the internal configuration of the ultrasonic diagnostic unit main body; and FIG. 3 illustrates an ultrasonic probe connected to the ultrasonic diagnostic unit main body of FIG. 1.

DETAILED DESCRIPTION OF THE PREFERRED EMBODIMENTS

Although this invention is applicable to numerous and various types of medical units, it has been found particularly useful in the environment of ultrasonic diagnostic units. Therefore, without limiting the applicability of the invention to ultrasonic diagnostic units, the invention will be described in such environment.

Figure 1:
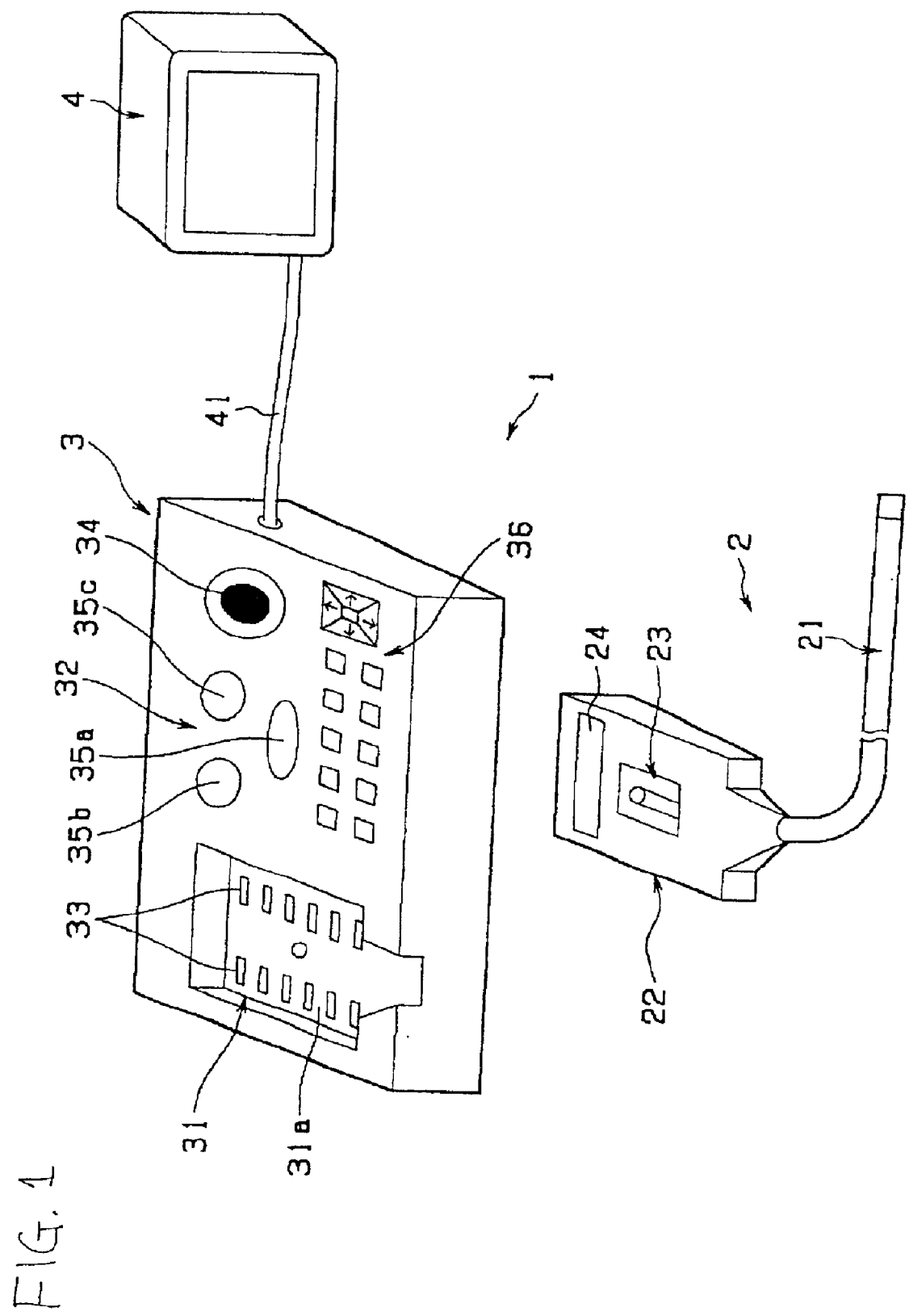
FIGS. 1 through 3 illustrate an embodiment of the medical unit of the present invention where.
Figure 2:
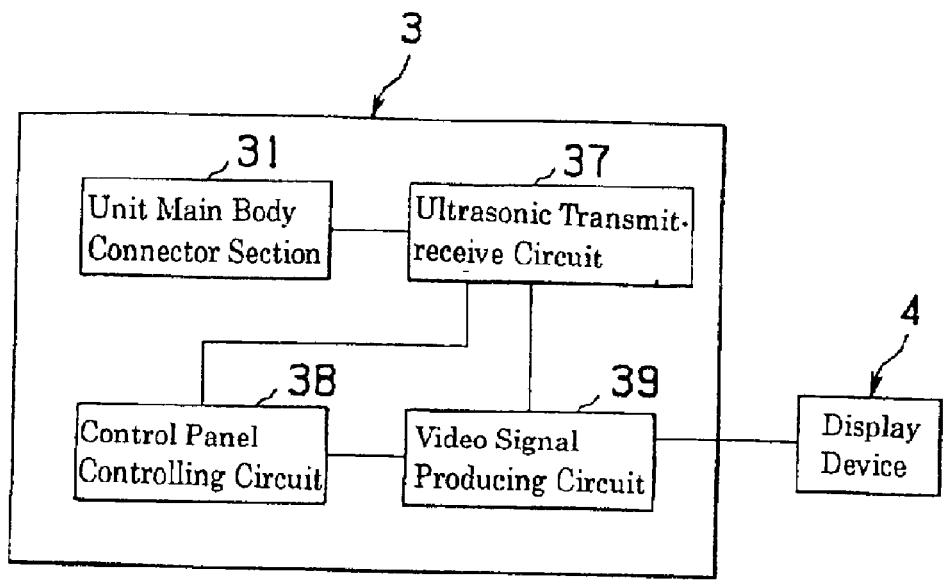
Figure 3:
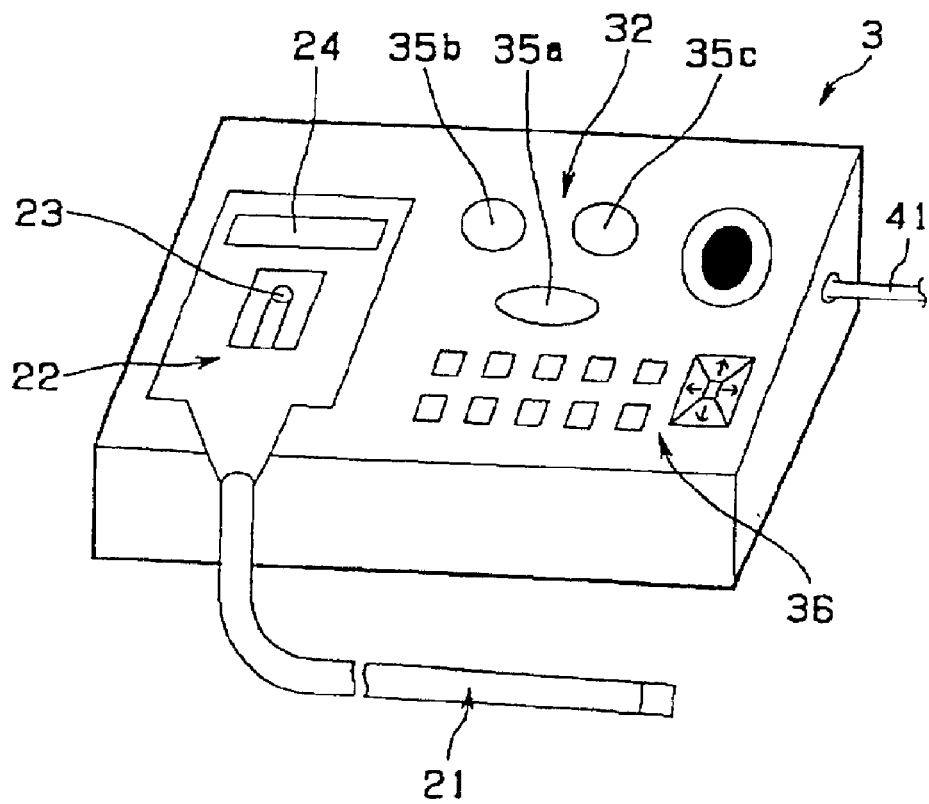

Referring now to FIGS. 1–3, a first embodiment of the medical unit according to the present invention will be described. As shown in FIG. 1, the ultrasonic diagnostic unit 1 according to the present embodiment comprises an ultrasonic probe 2, an ultrasonic diagnostic unit main body 3 (hereinafter referred to as "diagnostic unit main body") to which the ultrasonic probe 2 is connected, and a display device 4 that can display ultrasonic diagnostic images. Although in the present embodiment, the display device is designed to be separated from the ultrasonic diagnostic unit main body, the display device may be integrated into the ultrasonic diagnostic unit main body.

The ultrasonic probe 2 has an insertion section 21 that is inserted into a body cavity, a probe element (not shown) embedded in the distal section of the insertion section, and a probe connector section 22 disposed on the proximal section of the insertion section 21 as an electric connection section. An electric contact point (not shown) is arranged on the probe connector section 22. The diagnostic unit main body 3 includes a unit main body connector section 31, to which the probe connector section 22 is removably connected, and an ultrasonic transmit-receive circuit to produce ultrasonic driving signals and process ultrasonic signals. The display device is connected to the diagnostic unit main body 3 via an image cable 41.

A control panel 32 is arranged on the upper face of the diagnostic unit main body 3. The control panel 32 allows a user to control and direct external devices including the unit main body connector section 31, ultrasonic probe 2, and display device 4. The control panel 32 is preferably comprised of waterproof or water-resistant members including a waterproof sheet-like switch.

The control panel 32 is, for example, comprised of a power switch 34, various switches including a gain switch 35a for adjusting the amplification degree of ultrasonic echo, and a freeze switch 35b for stopping ultrasonic image updating, a keyboard switch 36 for alphanumeric character, katakana, hiragana, etc.

The unit main body connector section 31 and control panel 32 are arranged side by side. The unit main body connector 31 has a concave shape substantially corresponding to that of the probe connector section 22 of the ultrasonic probe 2. The unit main body connector 31 further has plural electric contact points 33 electrically conducting to corresponding electric contact points of the probe connector section 22 arranged on the bottom face 31a of the concave section of the probe connector section 22. Thus, as shown in FIG. 3, the probe connector section 22 is designed to be attached to or removed from the unit main body connector section 31 in a direction substantially vertical to the upper face of the diagnostic unit main body 3.

In the present embodiment, since the control panel 32 is situated in the upper part of the ultrasonic diagnostic unit 1, the unit main body connector section 31 is also arranged in the upper part of the ultrasonic diagnostic unit 1.

Figure 4:
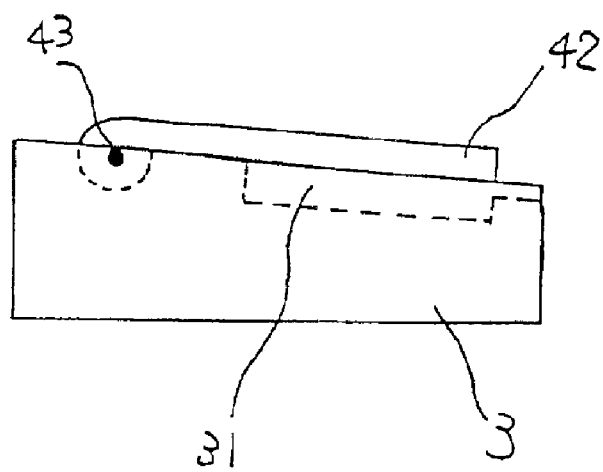
FIG. 4 illustrates a cover positioned on the ultrasonic diagnostic unit main body of FIG. 1 in a closed position.
Figure 5:
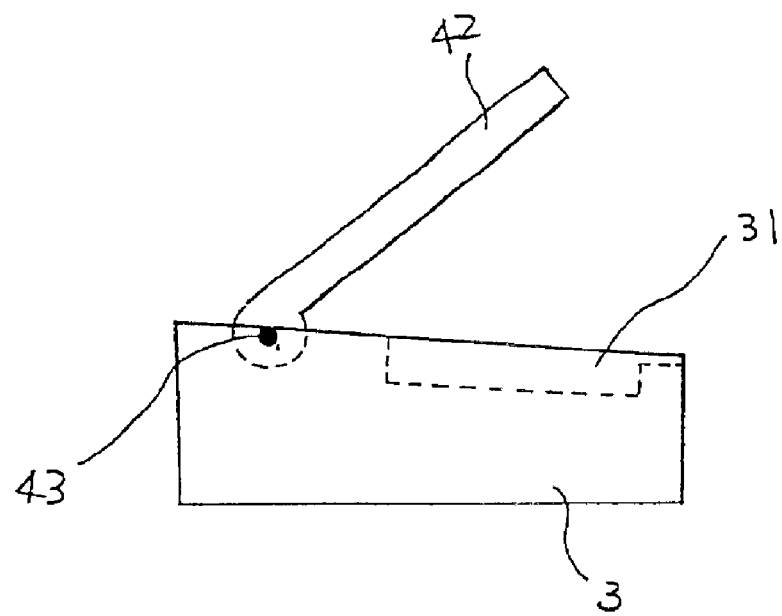
FIG. 5 illustrates a cover positioned on the ultrasonic diagnostic unit main body of FIG. 1 in an open position.

As shown in FIGS. 4 and 5, a cover 42 is arranged over the unit main body connector section 31 to cover it, and can be opened and closed with respect to axis 43. At least a portion of the cover 42 is formed out of transparent material. The cover 42 is designed to be shut while the probe connector 22 is connected to the unit main body connector section 31. With the cover 42 closed, dust or water cannot easily infiltrate into the unit main body connector section 31.

Moreover, a control section (not shown) is embedded in the ultrasonic diagnostic unit to terminate the passage of electric current to the unit main body connector section 31. The control section has a detection means (not shown) to detect the cover 42 opening or closing. The detection means may be a well-known optical sensor or contact sensor, which allows terminating the passage of electric current to the unit main body connector section 31 when the cover 42 is closed. Therefore, electric contact points on the unit main body connector section 31 are protected from shorts.

Referring back to FIG. 3, a knob section 23 is preferably arranged on the probe connector section 22. The knob section 23 allows the probe connector section 22 to be attached to and removed from the unit main body connector section 31. By appropriately operating the knob section 23, the probe connector section 22 can either be fixedly retained to or removed from the unit main body connector section 31.

In addition, an information display section 24 is arranged on the probe connector section 22. The information display section 24 is an identifying means for identifying the kind of the ultrasonic probe 2, and in the present embodiment, probe information including frequency is specified. The information display section is situated near the control panel 32 when the probe connector 22 is connected to the unit main body connector section 31. Since the cover 42 is transparent, the information display section 24 can be viewed from the outside even when the cover 42 is in a closed position. Although in the present embodiment, the cover is preferably transparent as a whole, only a portion corresponding to the information display section may be formed out of transparent material.

As shown in FIG. 2, the size of the diagnostic unit main body 3 can be miniaturized using high-density mounting technology such as IC technology. In the diagnostic unit main body 3, are arranged an ultrasonic transmit-receive circuit 37 for transmitting and receiving ultrasonic signals, and forming beams, via the probe connector section 22 connected to the unit main body connector section 31, a control panel controlling circuit 38 connected to various switches 34, 35a, 35b, etc. on the control panel 32, and a video signal producing circuit 39 for producing video signals (image signals) from electric signals transmitted from the ultrasonic transmit-receive circuit 37 and outputting them.

The operation of the ultrasonic diagnostic unit 1 of the present invention will now be described with reference to FIGS. 1–3.

At first, the surgeon selects an ultrasonic probe 2, and the probe connector section 22 of the ultrasonic probe 2 is fit in the unit main body connector section 31. And, by operating the knob section 23, the probe connector section 22 is fixedly retained to the unit main body connector section 31.

Next, the power switch 34 arranged on the diagnostic unit main body 3 is turned on, and switches 34, 35a, 35b, etc. on the control panel 32 are appropriately operated. This allows control signals to be transmitted from the control panel controlling circuit 38 to the ultrasonic transmit-receive circuit 37. Thus, it is possible to control the ultrasonic functions to adjust the amplification degree of echo signals, or to stop transmitting and receiving ultrasonic waves, for example.

Next, ultrasonic diagnosis starts. Ultrasonic signals are transmitted from the ultrasonic probe element (not shown), while reflected echo signals are received by the ultrasonic probe element. After being amplified, the received echo signals are converted into digital signals thorough an A/D converter (not shown), and formed into beams through a digital delay circuit (not shown). Those signals formed into beams are processed through a digital filter (not shown), and through the video signal producing circuit 39, converted into video signals which are output to the display device 4 or a printer (not shown).

When the ultrasonic probe 2 is replaced with another type probe (not shown) as necessary, the knob section 23 of the probe connector section 22 fixedly retained on the diagnostic unit main body 3 is operated to remove the ultrasonic probe 2. The probe connector section 22 can then be removed from the diagnostic unit main body 23. And, the replacement process is finished by arranging and fixedly retaining the probe connector section of another type ultrasonic probe on the unit main body connector section 31.

During examination, the surgeon can confirm the kind of ultrasonic probe by viewing the information display section 24 or display device 4 near the control panel 32. Although in the present embodiment, a single unit main body connector section 31 is arranged on the diagnostic unit main body 3, plural main body connector sections 31 may be so arranged.

Since in this way, the unit main body connector section to which the probe connector section of the ultrasonic probe is connected is arranged near the control panel of the ultrasonic diagnostic unit main body in a plane of the same direction as the control panel, it is easy to replace the ultrasonic probe with another.

In addition, even when the ultrasonic diagnostic unit main body has only one unit main body connector section, it is easy to replace the ultrasonic probe with another. Furthermore, by viewing the information display section arranged on the probe connector section of the ultrasonic probe, the user can easily identify the kind of the ultrasonic probe connected to the ultrasonic diagnostic unit main body.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

I claim:

1. A medical unit comprising:
    an ultrasonic probe having a probe element at its distal end and an electrical connection section at its proximal end; and
    an ultrasonic diagnostic unit main body having an upper face and a circuit therein for processing ultrasonic signals transmitted from said ultrasonic probe element, said ultrasonic unit main body further including an input means arranged on said upper face and connected to said circuit, and a connected section to which said electrical connection section is connected, said electric connection section is attached to and removed from said connected section in a direction substantially vertical to said upper face,
    wherein said connected section has a first electrical contact point and said electrical connection section has a second electrical contact point to be connected to said first electrical point,
    wherein said ultrasonic probe further includes a probe upper face which is turned upward when said electrical connection section is connected to said connected section, and an identifying means which is arranged on said probe upper face so that the kind of said ultrasonic probe can be identified by visual inspection.

2. The medical unit according to claim 1 wherein said ultrasonic diagnostic unit main body has a cover with which said connected section is covered.

3. The medical unit according to claim 2 wherein said connected section can be covered with said cover while said electric connection section is connected to said connected section, at least a portion of said cover corresponding to said identifying means being transparent.

4. A medical unit comprising:
    an ultrasonic probe having a probe element at its distal end and an electrical connection section at its proximal end; and
    an ultrasonic diagnostic unit main body having an upper face and a circuit therein for processing ultrasonic signals transmitted from said ultrasonic probe element, said ultrasonic unit main body further including an input means arranged on said upper face and connected to said circuit and a connected section to which said electrical connection section is connected, said electric connection section is attached to and removed from said connected section in a direction substantially vertical to said upper face,
    wherein said connected section has a first electrical contact point and said electrical connection section has a second electrical contact point to be connected to said first electrical point,
    wherein said ultrasonic diagnostic unit main body has a cover with which said connected section is covered,
    wherein said ultrasonic diagnostic unit main body has a control section for controlling the passage of electric current to said connected section, said control section passing electric current to said connected section when said connected section is covered with said cover, and stopping electric current to said connected section when said connected section is not covered with said cover.

5. A medical unit comprising:
    an ultrasonic probe having a probe element at a distal end of the ultrasonic probe and an electrical connection section at a proximal end of the ultrasonic probe; and
    an ultrasonic diagnostic unit main body having an upper face and a circuit therein for processing ultrasonic signals transmitted from said probe element, said ultrasonic diagnostic unit main body further including an input switch arranged on said upper face and connected to said circuit, and a connected section to which said electrical connection section is connected, said electric connection section is attached to and removed from said section in a direction substantially vertical to said upper face, wherein said connected section has a first electrical contact point, and said electrical connection section has a second electrical contact point for connection to said first electrical point, wherein said ultrasonic probe further includes a probe upper face which is turned upward when said electrical connection section is connected to said connected section, and an information display which is arranged on said probe upper face such that a type of said ultrasonic probe can be identified by a visual inspection.

6. The medical unit according to claim 5 wherein said ultrasonic diagnostic unit main body has a cover with which said connected section is covered.

7. The medical unit according to claim 6 wherein said connected section can be covered with said cover while said electric connection section is connected to said connected section, at least a portion of said cover corresponding to said information display being transparent.

8. A medical unit comprising:

an ultrasonic probe having a probe element at a distal end of the ultrasonic probe and an electrical connection section at a proximal end of the ultrasonic probe; and an ultrasonic diagnostic unit main body having an upper face and a circuit therein for processing ultrasonic signals transmitted from said ultrasonic probe element, said ultrasonic diagnostic unit main body further including an input switch arranged on said upper face and connected to said circuit, and a connected section to which said electrical connection section is connected, said electrical connection section is attached to and removed from said connected section in a direction substantially vertical to said upper face;

wherein said connected section has a first electrical contact point, and said electrical connection section has a second electrical contact point for connection to said first electrical point, wherein said ultrasonic diagnostic unit main body has a cover with which said connected section is covered, wherein said ultrasonic diagnostic unit main body has a control section for controlling the passage of electric current to said connected section, said control section passing electric current to said connected section when said connected section is covered with said cover, and stopping electric current to said connected section when said connected section is not covered with said cover.

* * * * *